(12) United States Patent
Cinthio et al.

(10) Patent No.: US 11,850,097 B2
(45) Date of Patent: Dec. 26, 2023

(54) MAGNETOMOTIVE PROBE SYSTEM AND METHOD OF USE THEREOF

(71) Applicant: NanoEcho AB, Lund (SE)

(72) Inventors: Magnus Cinthio, Höör (SE); Maria Evertsson, Lund (SE); Tomas Jansson, Lund (SE); Hans Persson, Lund (SE); Fredrik Olsson, Kävlinge (SE); Sarah Fredriksson, Dalby (SE)

(73) Assignee: NanoEcho AB, Lund (SE)

( * ) Notice: Subject to any disclaimer, the term of this patent is extended or adjusted under 35 U.S.C. 154(b) by 955 days.

(21) Appl. No.: 16/358,462

(22) Filed: Mar. 19, 2019

(65) Prior Publication Data
US 2019/0209135 A1 Jul. 11, 2019

Related U.S. Application Data

(63) Continuation of application No. 14/888,404, filed as application No. PCT/EP2014/059248 on May 6, 2014, now abandoned.

(30) Foreign Application Priority Data

May 6, 2013 (EP) .................................... 13166681

(51) Int. Cl.
A61B 8/08 (2006.01)
A61B 8/00 (2006.01)
A61B 5/0515 (2021.01)

(52) U.S. Cl.
CPC ............ *A61B 8/481* (2013.01); *A61B 5/0515* (2013.01); *A61B 8/4209* (2013.01);
(Continued)

(58) Field of Classification Search
CPC ............ G01N 29/265; G01N 29/2291; G01N 29/0422; G01N 29/28; A61B 8/481;
(Continued)

(56) References Cited

U.S. PATENT DOCUMENTS 5,844,140 A * 12/1998 Seale ................. G01N 29/2456
73/620
5,919,139 A 7/1999 Lin
(Continued)

FOREIGN PATENT DOCUMENTS

JP H11-12390 A 5/1999
JP 2007-105351 A 4/2007
WO WO 2012/160541 A2 11/2012

OTHER PUBLICATIONS

Japan Patent Office, Official Action dated Nov. 6, 2020 in Japanese Patent Application No. 2019-142707 with English Translation, 9 pages.
(Continued)

*Primary Examiner* — Baisakhi Roy
(74) *Attorney, Agent, or Firm* — Inskeep IP Group, Inc.

(57) ABSTRACT

A magnetomotive imaging probe system is disclosed comprising a movable probe, a magnet arranged on the probe, and an ultra sound transducer, wherein the magnet is arranged to generate a time-varying magnetic field (T) at an imaging plane (304) of the ultrasound transducer, distally of the ultra sound transducer and the probe, when the probe has a proximal first position adjacent the ultra sound transducer.

15 Claims, 12 Drawing Sheets

(52) U.S. Cl.
CPC .......... *A61B 8/4455* (2013.01); *A61B 8/4483* (2013.01); *A61B 8/54* (2013.01)

(58) Field of Classification Search
CPC ....... A61B 8/54; A61B 8/4483; A61B 8/4455; A61B 8/4209; A61B 5/0515
See application file for complete search history.

(56) References Cited

U.S. PATENT DOCUMENTS

| | | | | |
|---|---|---|---|---|
| 6,198,956 | B1* | 3/2001 | Dunne | A61B 8/4281 |
| | | | | 600/407 |
| 7,731,661 | B2 | 6/2010 | Salcudean et al. | |
| 2006/0053892 | A1* | 3/2006 | Georgeson | G01N 29/28 |
| | | | | 73/634 |
| 2006/0055396 | A1* | 3/2006 | Georgeson | G01N 29/265 |
| | | | | 324/202 |
| 2006/0055399 | A1* | 3/2006 | Georgeson | G01N 29/28 |
| | | | | 324/232 |
| 2007/0215553 | A1* | 9/2007 | Yellen | B01F 13/0809 |
| | | | | 210/695 |
| 2009/0185166 | A1* | 7/2009 | Oldenburg | A61B 5/0051 |
| | | | | 356/72 |
| 2010/0108578 | A1* | 5/2010 | Dittmer | B03C 1/32 |
| | | | | 209/636 |
| 2011/0306870 | A1 | 12/2011 | Kuhn | |
| 2012/0226093 | A1* | 9/2012 | Creighton | A61K 38/482 |
| | | | | 977/773 |
| 2014/0257104 | A1* | 9/2014 | Dunbar | A61B 8/14 |
| | | | | 600/443 |
| 2015/0230810 | A1* | 8/2015 | Creighton | A61K 41/0028 |
| | | | | 604/518 |

OTHER PUBLICATIONS

Japan Patent Office, Official Action dated January in Japanese Patent Application No. 2016-512346, 5 pages.
Japan Patent Office, Official Action dated January in Japanese Patent Application No. 2016-512346 with English translation, 7 pages.
WIPO, International Preliminary Examining Authority (European Patent Office), International Preliminary Report on Patentability dated Aug. 7, 2015 in International Patent Application No. PCT/EP2014/059248, 25 pages.
WIPO, European International Search Authority, International Search Report dated Aug. 8, 2015 in International Patent Application No. PCT/EP2014/059248, 6 pages.
Evertsson, M. et al., "Frequency- and phase-sensitive magnetomotie ultrasound imaging of superparamagnetic iron oxide nanoparticles," *IEEE Transactions On Ultrasonics, Ferroelectrics And Frequency Control*, vol. 60,No. 3, IEEE, Mar. 2, 2013, pp. 481-491.
Congxian, J. et al., "Dynamic manipulation of magnetic contrast agents in photoacoustic imaging," *Photons Plus Ultrasound: Imaging And Sensing* 2011, vol. 7899, No. 1, SPIE, Feb. 10, 2011, pp. 1-6.
Japan Patent Office, Official Action dated Aug. 21, 2018 in Japanese Patent Application No. 2016-512346 with English Translation, 7 pages.
Japan Patent Office, Official Action dated Apr. 28, 2020 in Japanese Patent Application No. 2019-142707 with English Translation, 6 pages.
Canada Patent Office, Office Action dated Feb. 17, 2022 in Canadian Patent Application No. 2,911,289, 4 pages.

* cited by examiner

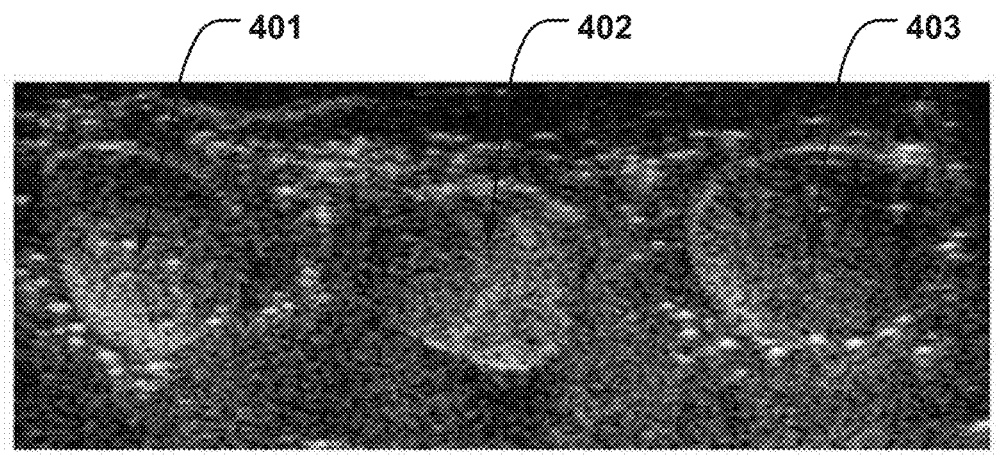
Fig. 7a
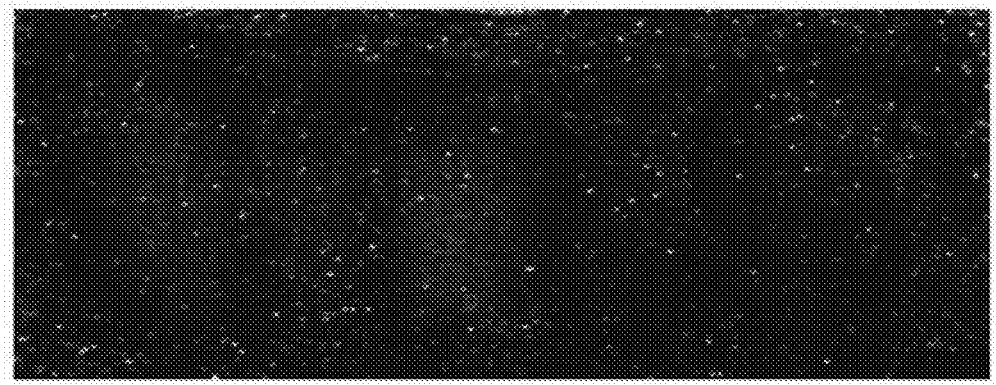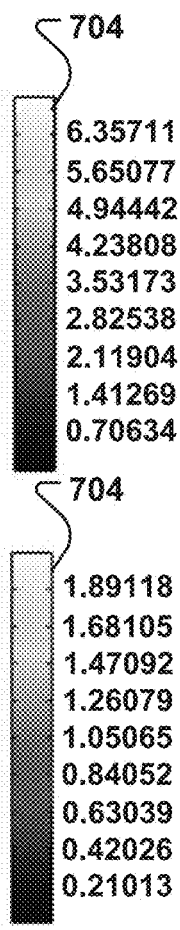
Fig. 7b
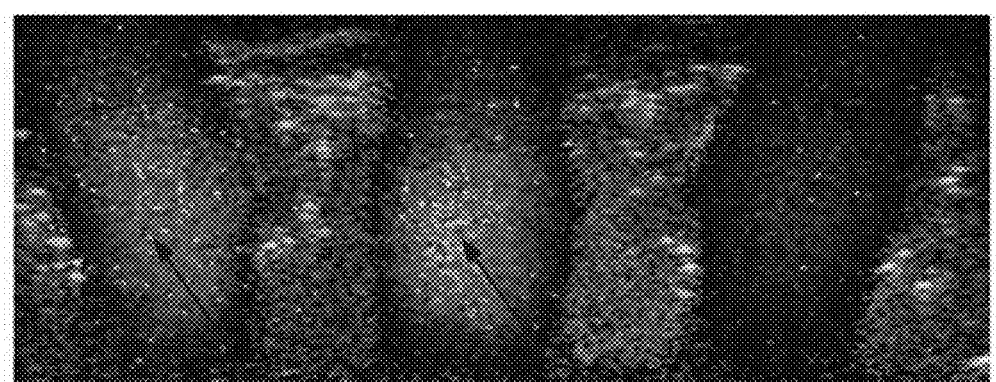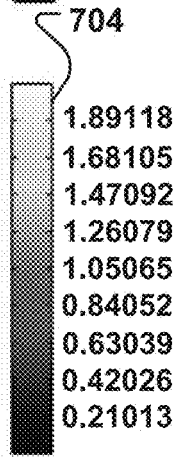
Fig. 7c
Fig. 7

MAGNETOMOTIVE PROBE SYSTEM AND METHOD OF USE THEREOF

RELATED APPLICATIONS

This application is a continuation of U.S. patent application Ser. No. 14/888,404, filed Oct. 30, 2015, which is the U.S. National Phase of and claims priority to International Patent Application No. PCT/EP2014/059248, International Filing Date May 6, 2014, entitled Magnetomotive Probe System And Method Of Use Thereof, which claims benefit of European Patent Application No. 13166681.0, filed May 6, 2013 entitled Magnetomotive Probe Assembly And Method Of Use Thereof, all of which are incorporated herein by reference in their entireties.

FIELD OF THE INVENTION

This invention pertains in general to the field of magnetomotive imaging. More particularly the invention relates to a magnetomotive imaging probe system, a magnetomotive imaging probe assembly, and a method of magnetomotive imaging with such imaging probe system or assembly.

BACKGROUND OF THE INVENTION

Magnetomotive imaging is a new imaging technique where superparamagnetic iron oxide nanoparticles can be used as ultrasound contrast agents. The main idea of this imaging technique is the application of a time-varying magnetic field (pulsed or sinusoidal) to the volume where the nanoparticles are deposited. The magnetic field induces movement of the particles and thereby the surrounding tissue. Previous techniques, such as disclosed in Evertsson, M. et al, IEEE, Transactions on ultrasonic, ferroelectrics, and frequency control, vol. 60, no. 3, 1 Mar. 2013, pages 481-491, that has been used to create the time-varying magnetic field has been employing an electromagnet, which consists of a coil around a cone-shaped iron-core, see FIG. 1. When a current is applied, a magnetic field is formed from the tip of the core. The force acting on the particles is dependent on the field strength, and on the field gradient. A problem with such previous techniques is that the displacement amplitude of the nanoparticle-laden regions is higher closer to the tip, and the resulting image data therefore gives misleading information about the nanoparticle concentration. This inevitable leads to problems in providing accurate analysis of the properties of the material or tissue in which the nanoparticles has been collected, e.g. in the situation where the nanoparticles have been labeled with tumor- or tissue specific targeting agents. The information available for e.g. detecting cancer in tissue therefore becomes flawed. Problems with prior art thus includes insufficient accuracy in detecting these targeting nanoparticles, and consequently insufficient accuracy in detecting, resolving and analyzing the material which the nanoparticles targets and binds.

Further problems with prior art is that the tissue which is analyzed is affected by the analyzing equipment, for example by heat, which also decreases the possibilities for performing a complete analysis of the tissue.

Jia Congxian et al, Photons plus ultrasound: Imaging and sensing, 2011, Proc. of SPIE, vol. 7899, no. 1, 10 Feb. 2011, discloses a method for magnetomotive photoacoustic imaging where magnetic particles in a tube where placed in a water tank containing magnets for manipulation of the particles, and an ultrasound device placed on top of the water tank. Thus another problem with prior art is the unsuitability of these setups for applications in humans or larger animals due to restrictions or limitations in positioning the various components such as the magnet in relation to the ultrasound transducer.

Problems with prior art, if at all possible to implement, may accordingly lead to reduced patient safety, more time consuming and expensive diagnosis, and less possibilities for an individualized treatment in the patient care.

Hence an improved device or assembly, and/or system, and method, for providing improved magnetomotive imaging would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a magnetomotive imaging probe assembly and a method for magnetomotive imaging with a probe assembly according to the appended patent claims.

According to a first aspect of the invention a magnetomotive imaging probe system is provided comprising a movable probe, a magnet arranged on the probe, and an ultra sound transducer, wherein the magnet is arranged to generate a time-varying magnetic field (T) at an imaging plane (304) of the ultrasound transducer, distally of the ultra sound transducer and the probe, when the probe has a proximal first position adjacent the ultra sound transducer.

According to a second aspect of the invention, a method of magnetomotive imaging with a probe system is provided, the system comprising a movable probe, an ultra sound transducer, and a magnet arranged on the probe. The method comprises positioning the probe at a proximal first position adjacent the ultra sound transducer, generating, with said magnet, a time-varying magnetic field (T) at an imaging plane of the ultrasound transducer, distally of the ultra sound transducer and the probe, and detecting motion of magnetic nanoparticles in response to said time-varying magnetic field with the ultrasound transducer in the imaging plane.

According to a third aspect of the invention, a magnetomotive imaging probe assembly is provided comprising a probe support and a magnet arranged on said probe support. The probe support is adapted to connect to an ultra sound transducer and fixate the position of the ultra sound transducer in relation to, and adjacent, the magnet, whereby in use the magnet is arranged to generate a time-varying magnetic field (T) at an imaging plane of the ultrasound transducer.

According to a fourth aspect of the invention, a method of magnetomotive imaging with a probe assembly is provided, the probe support being adapted to connect to an ultrasound transducer and having a magnet movably arranged on the probe support, the method comprising rotating the magnet to generate a time-varying magnetic field (T) at an imaging plane of the ultrasound transducer when connected to the probe support, and detecting a motion of magnetic nanoparticles in response to the time-varying magnetic field with the ultrasound transducer in the imaging plane.

According to another aspect of the invention, use of a magnetomotive imaging probe assembly or system according to the first or third aspect of the invention for magnetomotive ultrasound imaging of magnetic nanoparticles is provided.

Further embodiments of the invention are defined in the dependent claims, wherein features for the second and subsequent aspects of the invention are as for the first aspect mutatis mutandis.

Some embodiments of the invention provide for increased accuracy in resolving the concentration of nanoparticles in a material.

Some embodiments of the invention provide for increased accuracy in analyzing material properties in magnetomotive imaging.

Some embodiments of the invention provide for imaging that with less impact on the analyzed material.

Some embodiments of the invention provide for converting ultrasound imaging equipment to a magnetomotive imaging device.

Some embodiments of the invention provide for a compact and easy to use magnetomotive imaging probe assembly or system.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 7a-c are schematic illustrations of results obtained according to prior art;

DESCRIPTION OF EMBODIMENTS

Figure 1:
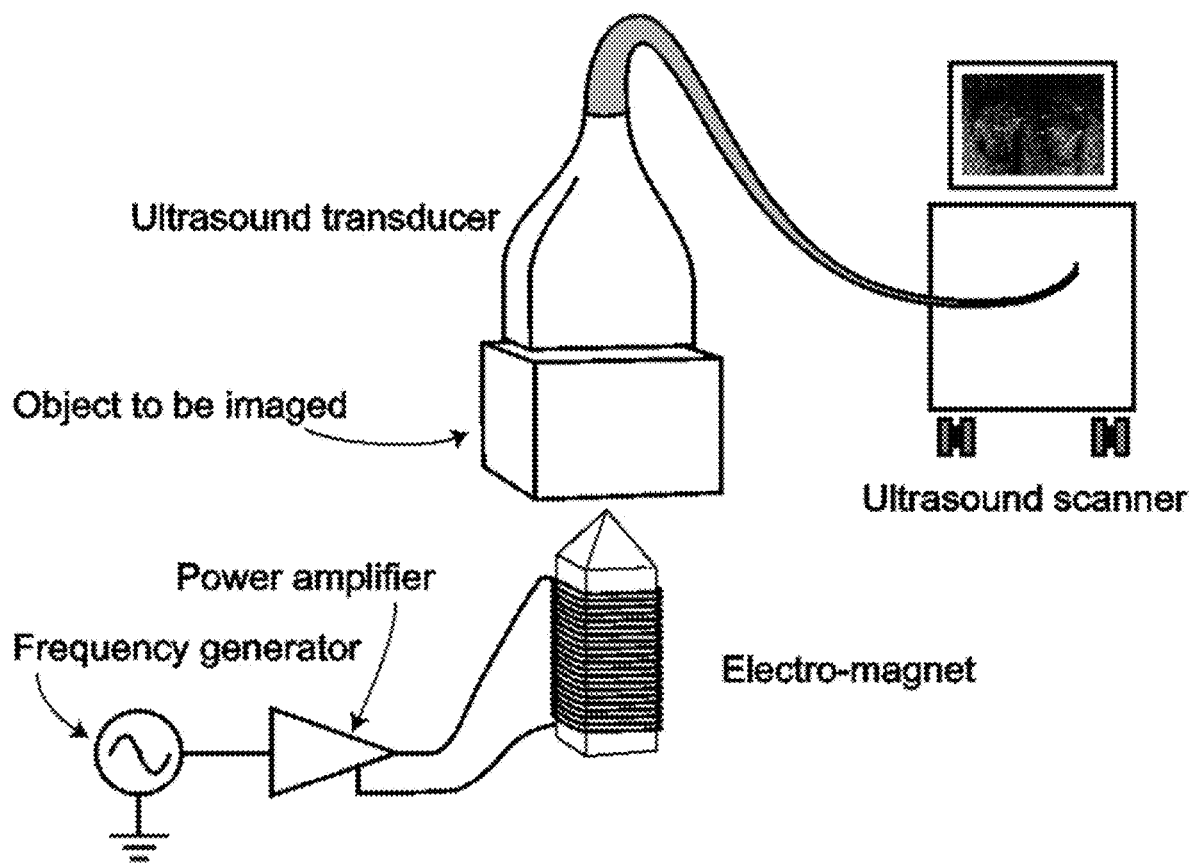
FIG. 1 is an illustration of prior art.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a probe assembly for magnetomotive imaging. However, it will be appreciated that the invention is not limited to this application but may be applied to many other fields and applications.

FIG. 1 shows a prior art magnetomotive imaging setup as discussed in the background of invention.

Figure 2:
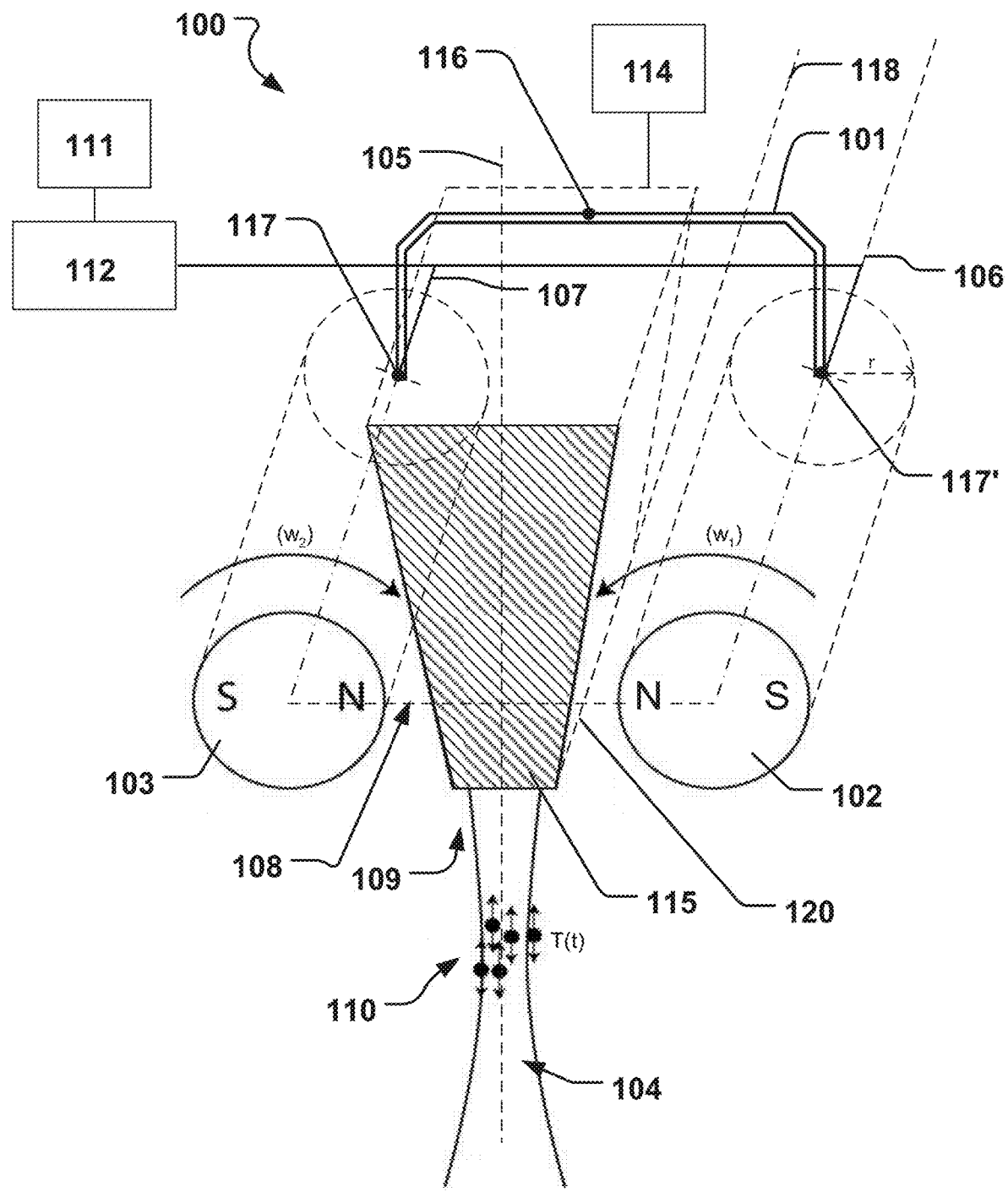
FIG. 2 is a schematic illustration of a magnetomotive imaging probe assembly according to an embodiment of the present invention.

FIG. 2 shows a magnetomotive imaging probe assembly 100 according to an embodiment of the invention. The probe assembly 100 comprises a probe support 101, and a magnet, 102, 103, arranged on the probe support 101. The probe support 101 is adapted to connect to an ultrasound transducer 115 and fixate the position of the ultrasound transducer 115 in relation to, and adjacent, the magnet 102, 103. The ultrasound transducer 115 may connect to the probe support in various ways, such as by a "snapping-in" function that provides for an engaging and disengaging connection, i.e. a releasable connection, and/or by using fixation means 116 to connect the probe support 101 to the ultrasound transducer 115. The magnet 102, 103, may be connected to the probe support 101 by a second fixation means 117, 117'. The magnet 102, 103, may thereby be fixed in relation to the ultrasound transducer 115 via the probe support 101. The probe support 101 may be adapted to connect to a variety of ultrasound transducers 115 by being shaped to conform to the geometries of such varying ultrasound transducers, i.e. ultrasound probes. In use, i.e. when the ultrasound transducer 115 is fixated by the probe support 101, the magnet 102, 103, is arranged to generate a time-varying magnetic field (T) at an imaging plane 104 of the ultrasound transducer 115. Due to the probe support 101 being arranged to fixate the position of the ultra sound transducer 115 adjacent the magnet 102, 103, a compact and versatile magnetomotive imaging probe assembly is provided, as the magnet 102, 103, and transducer 115 are integrated in the probe assembly 100 via the probe support 101. I.e. the magnet 102, 103, generates a time-varying magnetic field at the same location at the imaging plane 104 of the transducer wherever the probe 100 is positioned spatially relative the imaged subject. Imaging and analysis of tissue of humans and large animals is therefore possible without having to repeatedly repositioning the magnet to the current location of the ultra sound transducer as in the case with previous techniques. Indeed, the most hampering drawback with the prior techniques, is that the magnetic field is designed to emanate from the other side of the object to be imaged such as fixated at a position under the object, as seen in FIG. 1, or even more complex techniques where magnets are arranged on either side of the object and in fixed arrangement thereto, which does not allow for repositioning and/or imaging of larger objects. This makes currently proposed designs unsuitable for applications in humans or larger animals. Further, the larger and more powerful magnet of previous designs can be dispensed with as it is only necessary to provide a localized magnetic field at the position of the transducer, on contrary to having to provide a stronger field to cover a sufficient portion of the imaged object as in previous solutions. This allows for less interference with the imaged object, e.g. less heating issues during imaging. The previously described advantages may be provided with any type of magnet that is arranged to generate a time-varying magnetic field at the imaging plane 104 of the ultrasound transducer 115.

The magnet may be movably arranged on the probe support 101, and, whereby in use, the magnet 102, 103 may be arranged to generate the time-varying magnetic field (T) in response to a motion of the magnet 102, 103, relative the probe support 101 and the ultrasound transducer 115. The magnet 102, 103, may thus be movably connected to the probe support 101 such that it can provide such motion relative the ultrasound transducer 115, which is fixed in the probe support 101. Due to the motion of the magnet 102, 103, a time-varying magnetic field (T) is provided at a target location 110 in the imaging plane 104 of the ultrasonic transducer 115. Magnetic nanoparticles that are located at the target location 110 in the imaging plane 104 thus exhibits the fluctuations in the time-varying magnetic field (T) and are therefore forced to oscillate under the influence of the magnetic field (T). Because of the creation of the time-varying magnetic field in the axial direction 105 of the imaging plane 104 (see also FIG. 4b), the displacement amplitude of the nanoparticles can be detected by the ultrasonic transducer 115, when the probe assembly 101 is used to scan the object under examination. Imaging can thus be provided without the use of electromagnets. The magnet 102, 103, thus creates a time-varying magnetic field at the imaging plane 104 as it moves relative to the transducer 115. This provides for detection with high sensitivity as there is no need for applying a high current as for the prior art magnetomotive setup with an electromagnet, to achieve a strong magnetic field. Hence, there will be no problems with increased temperature which is the case when applying a high current trough an electromagnet. The probe assembly 101 thus allows for the analyzed sample to be less affected by the imaging probe and a more accurate analysis can be performed. Hence, the magnet 102, 103, may be a permanent magnet.

Figure 4A:
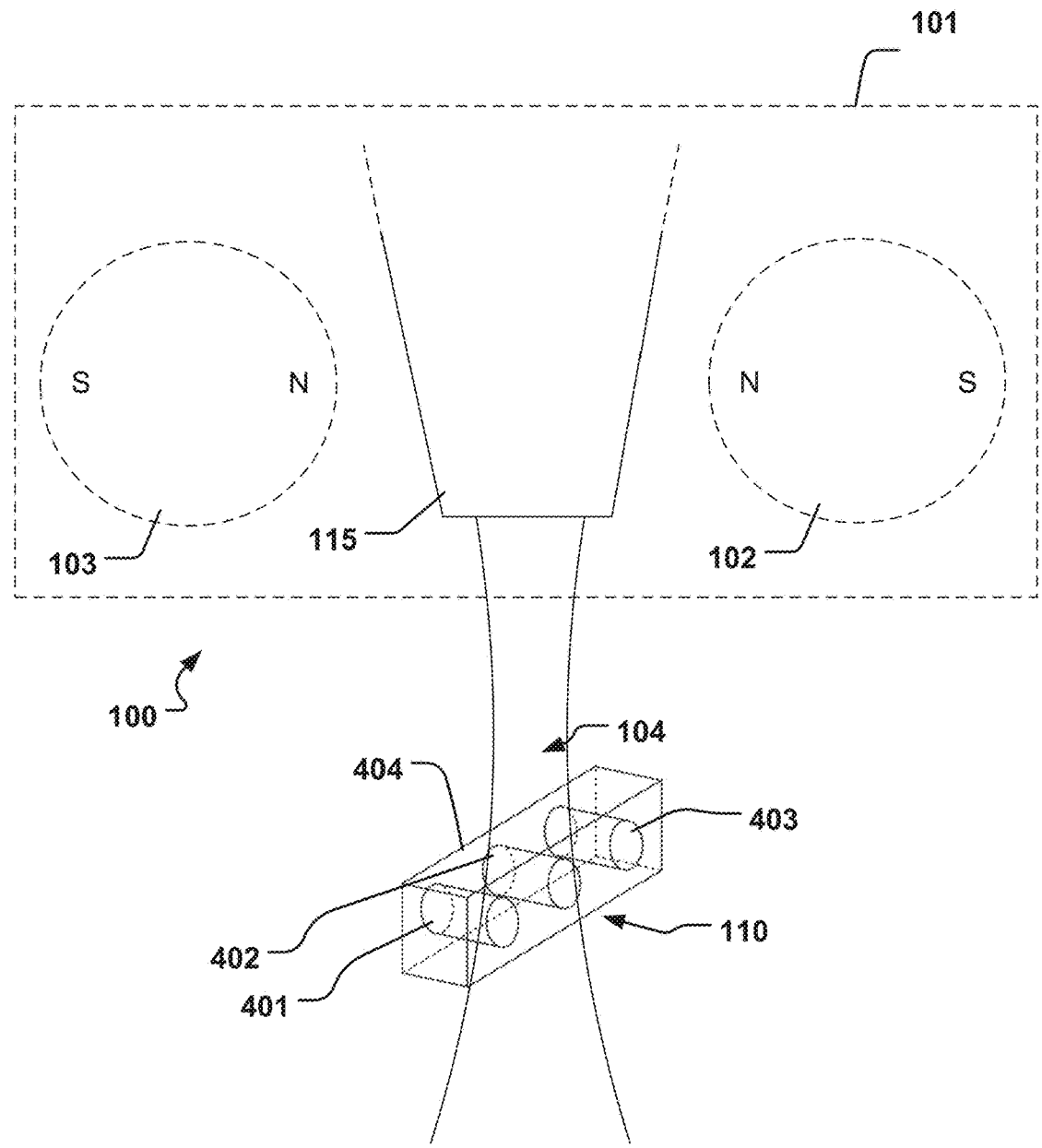
FIGS. 4a-b are schematic illustrations of a magnetomotive imaging probe assembly according to an embodiment of the present invention.
Figure 4B:
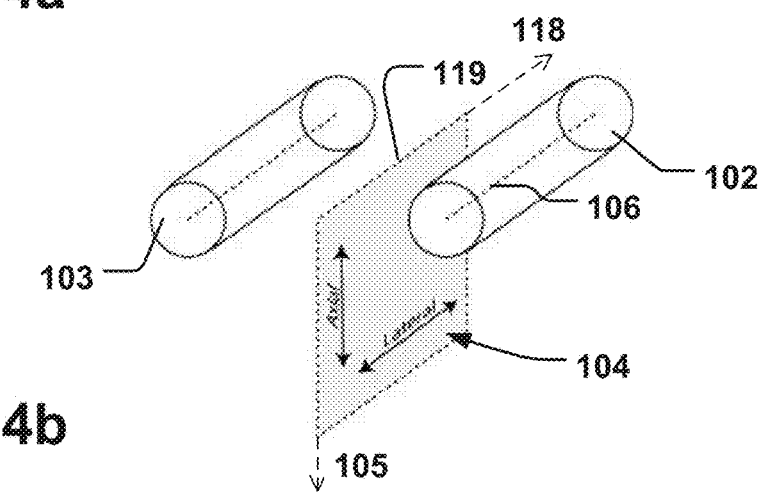
Figure 5A:
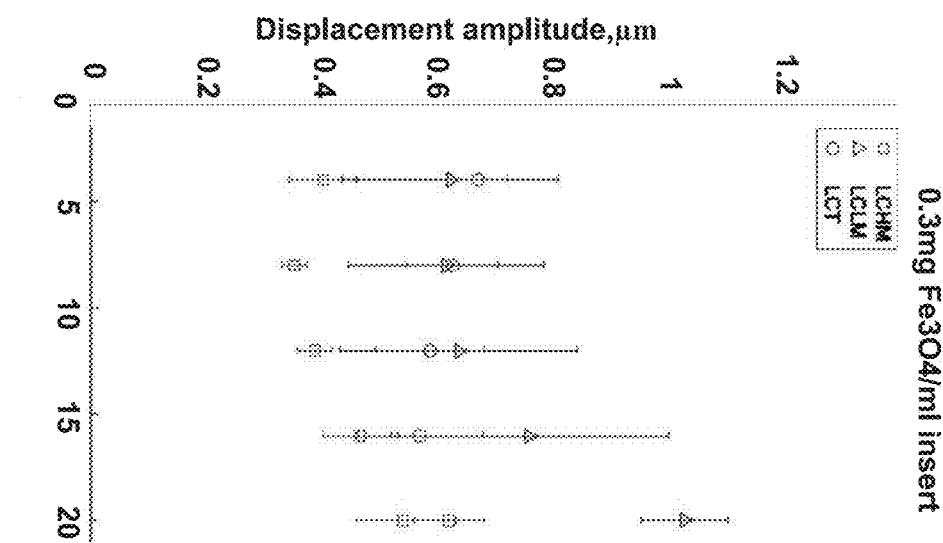
FIGS. 5a-f are schematic illustrations of results obtained according to an embodiment of the present invention.
Figure 5B:
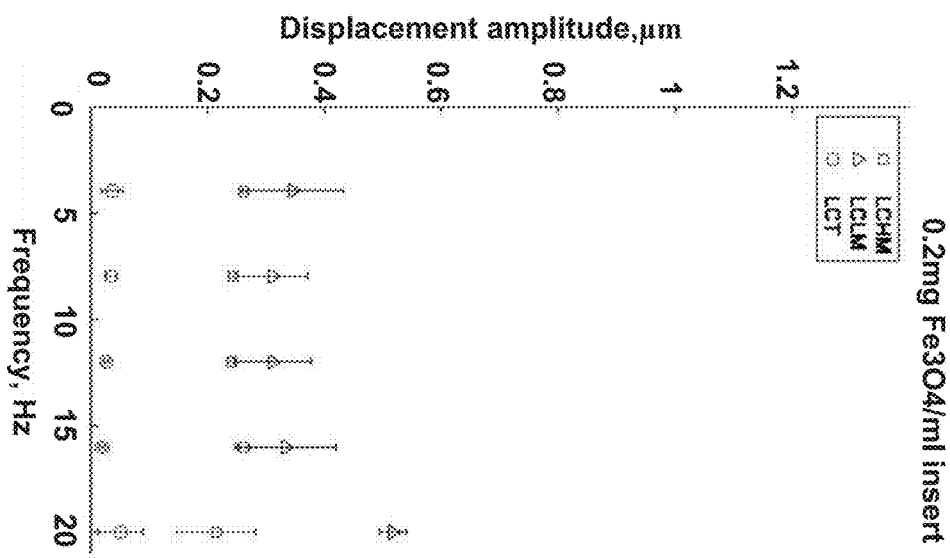
Figure 5C:
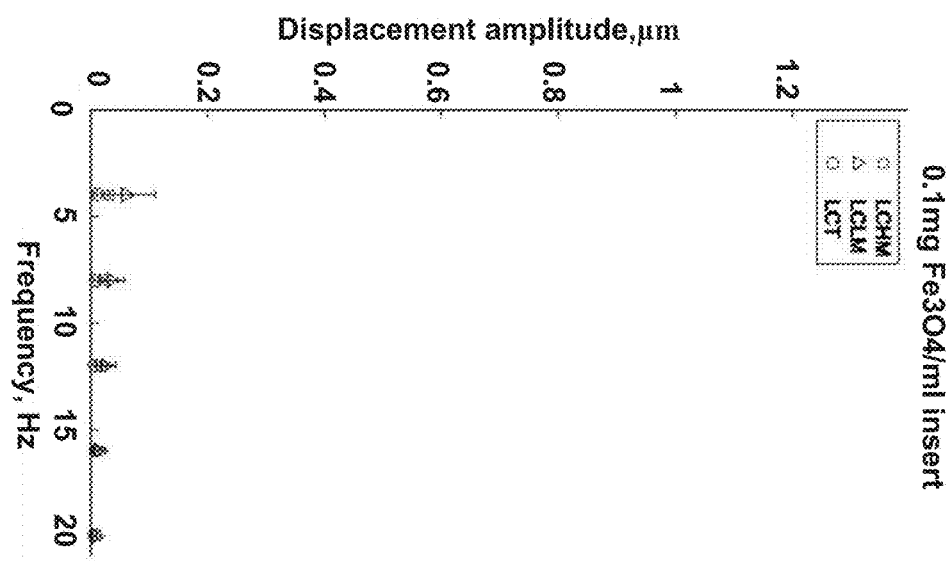
Figure 5D:
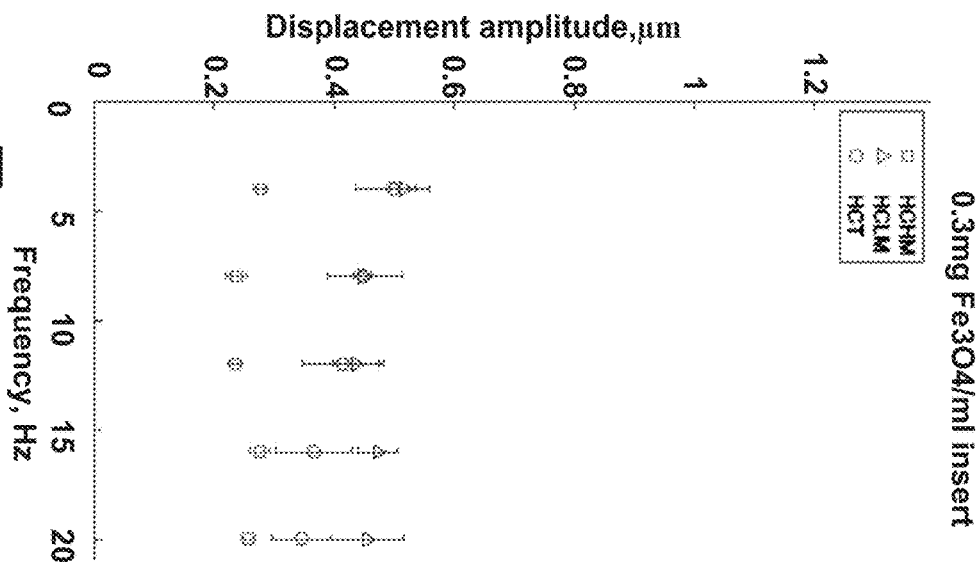
Figure 5E:
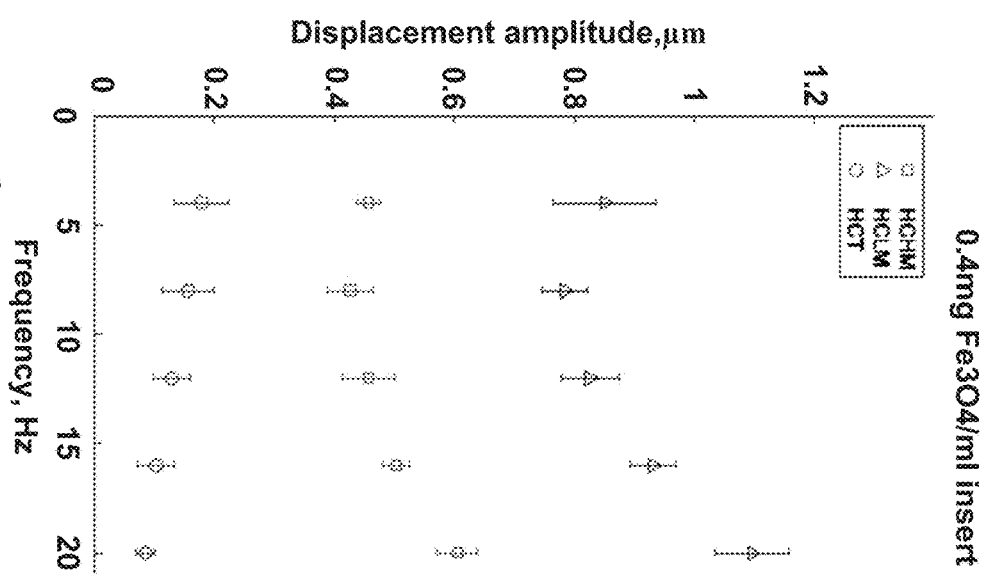
Figure 5F:
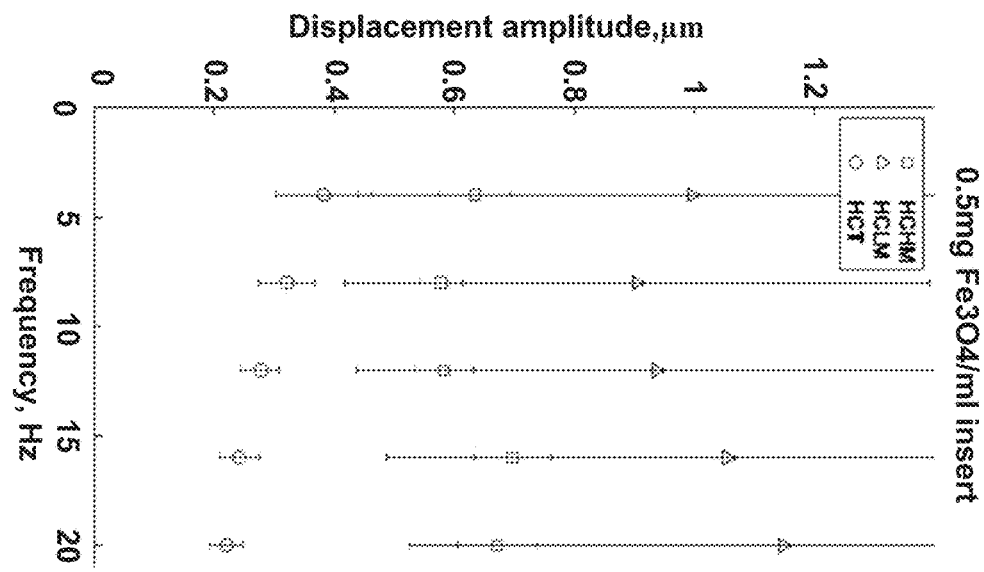

The magnet 102, 103, may be arranged on said support 101 to extend parallel to a lateral direction 118, as seen in FIG. 2 and FIG. 4b. The lateral direction 118 is perpendicular to the axial direction 105 of the imaging plane 104. The probe support 102 may be adapted to connect to, and fixate the position of, an ultrasound transducer 115 such that the width 119 of the imaging plane 104 extends in the lateral direction 118. The magnet 102, 103 may thus be arranged to extend along the width 119 of the imaging plane 104, as seen in FIGS. 2 and 4b. This removes previous problems with inhomogeneous magnetic fields in the lateral direction of the image plane that are created from fixating the tip of an electromagnets under the object to be imaged, which thereby, due to the dependency of the displacement amplitude of the nanoparticles on the field gradient from the tip, result in a larger displacement amplitude close to the position of the tip, compared to further away from the tip in the lateral direction, irrespectively of the actual concentration of the nanoparticles that is set out to be detected. This situation is illustrated in FIGS. 7a-c, where ultrasound and magnetomotive images on a tissue phantom are shown for a prior art magnetomotive imaging setup, such as illustrated in FIG. 1, using a magnetic solenoid excitation voltage at 4 Hz, 30 Vpp excitation voltage. The nanoparticle-laden inserts 401, 402, 403, as illustrated in FIG. 4a, are outlined in the figure, as well as the mapping of the detected nanoparticle concentration, c.f. FIG. 7c and scale 704 for indication of the detected concentration in the corresponding magnetomotive images 701, 702, 703, for the inserts 401, 402, 403. In more detail, the top row, FIG. 7a, shows ultrasonic B-mode images, and the middle row, FIG. 7b, show color-coded images representing displacement magnitude of the nanoparticles across the B-mode images. The middle row shows the total movement where the displacements at all frequencies are color-coded. The color of each pixel represents the displacement magnitude in that position and is coded according to the color bar scale 704 on the right of the FIGS. The bottom row, FIG. 7c, displays frequency tracked and phase-discriminative imaging, i.e. displacement was only color coded when occurring with frequency 8 Hz (two times the excitation frequency on the magnetic field) and the phase difference was less than ±1.15 radians relative to the center phase in the nanoparticle-laden regions. The concentration of nanoparticles in insert 401 is 0.5 mg $Fe_3O_4$ per ml, in insert 402 it is 0.3 mg $Fe_3O_4$ per ml, and in insert 403 it is 0.4 mg $Fe_3O_4$ per ml.

In particular from FIG. 7c, it can be clearly seen that in this prior art setup the movement of the inserts 401, 402, 403, moves towards the center of the image where the electromagnetic tip is located. The insert moving the most is therefore the middle one, i.e. insert 402, as seen from the corresponding magnetomotive image 702, which actually has the lowest concentration of nanoparticles (0.3 mg $Fe_3O_4$/ml). As mentioned before this is due to the inhomogeneous magnetic field, where the insert being closest to the tip of the electromagnet, which in this case is insert 402, has larger force acting on it compared to inserts 401 and 403. It is thus not possible to relate the measured displacement amplitude of the nanoparticles to properties such as the concentration of nanoparticles with this prior art setup, which can be crucial for performing an accurate and complete analysis of the targeted material.

Figure 8:
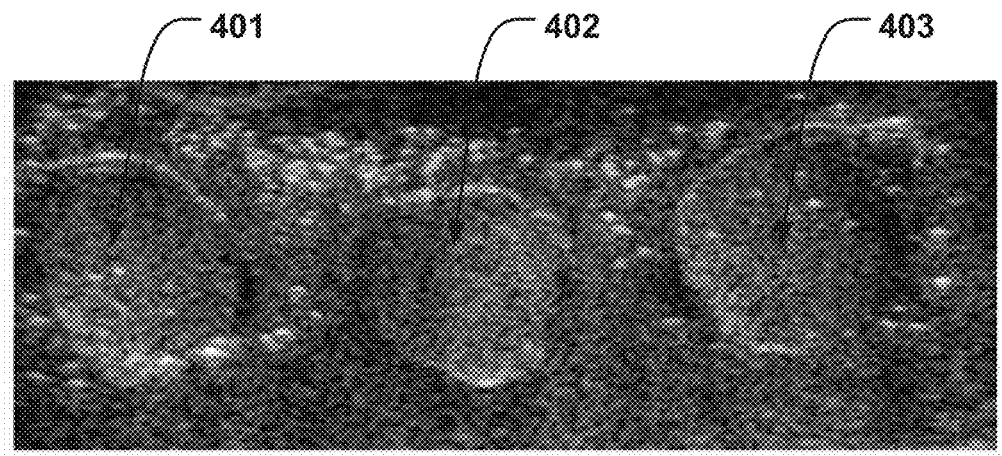
FIGS. 8a-c are a schematic illustrations of results obtained according to an embodiment of the present invention.
Figure 8:
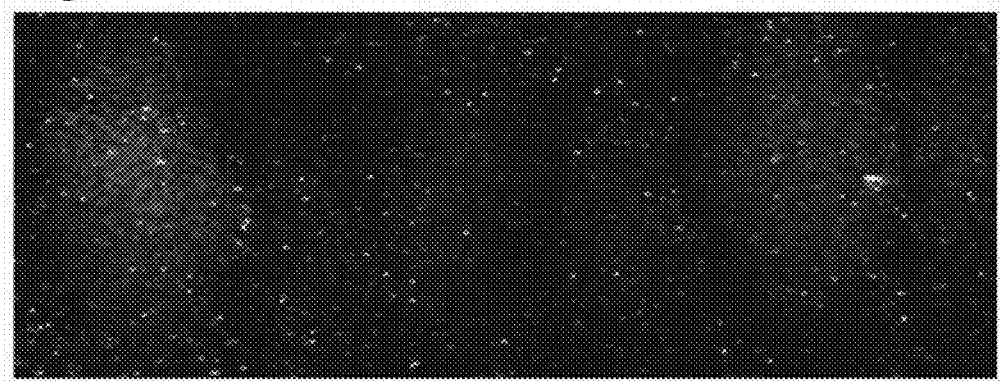
Figure 8:
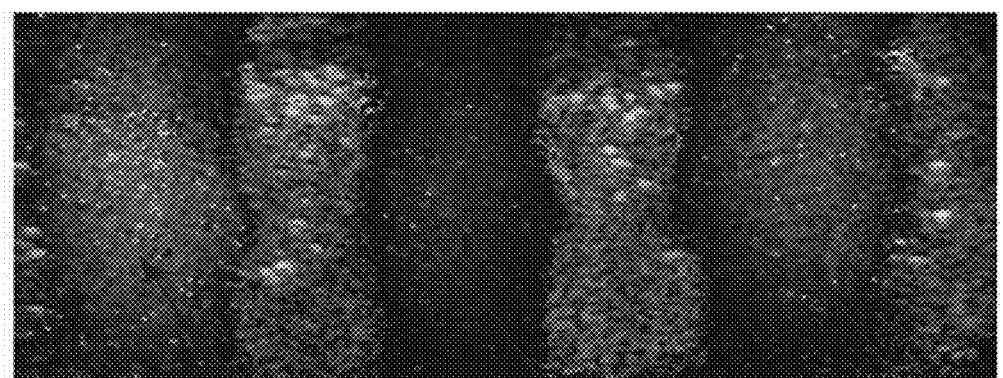

FIGS. 8a-c illustrates the corresponding magnetomotive images obtained from using the magnetomotive imaging probe assembly 101 according to the present invention. Due to the laterally homogeneous magnetic field created by the magnets 102, 103, arranged on the probe support to extend along the width 119 of the image plane 104 in the lateral direction 118 there is only movement of the nanoparticles parallel to the imaging plane 104 along the axial direction 105. Hence, the displacement of the nanoparticles gives an accurate representation of the concentration in the lateral direction 118, which now correctly reveals the left insert 401, outlined as object 801 in the corresponding magnetomotive image of FIG. 8c, as the insert having the highest concentration of nanoparticles (0.5 mg $Fe_3O_4$/l), and the right insert 403/803 as having the second highest concentration (0.4 mg $Fe_3O_4$/ml), and the middle insert 402/802 as having the lowest concentration (0.3 mg $Fe_3O_4$/ml). Hence, with the magnetomotive imaging probe assembly 100 the movement of the nanoparticles is increased with increasing nanoparticle concentration independent of the lateral position of the insert in the background material. The ultrasonic transducer 115 may have a distal edge 120, i.e. the transducer face. The probe support 101 may fixate the ultrasound transducer such that the distal edge 120 is arranged substantially parallel to the magnet 102, 103, and the lateral direction 118, and/or substantially parallel to the plane 108.

The previously described advantages may be provided with any type of magnet that is arranged to extend along the width of the image plane 104, parallel to lateral direction 118, and generating a time-varying magnetic field at the imaging plane 104 of the ultrasound transducer 115. In the examples in FIGS. 2-4, the magnet 102, 103, is movably arranged on the probe support 101 and is arranged to generate the time-varying magnetic field (T) being homogeneous in the lateral direction in response to a motion of the magnet relative the probe support 101 and the ultrasound transducer 115.

The setup of the magnetomotive probe assembly 100 is illustrated in FIG. 4, showing the cylindrical inserts 401, 402, 403, with different nanoparticle concentrations positioned in a tissue phantom 404, in relation to a target imaging location 110 of the probe assembly 100.

Figure 6:
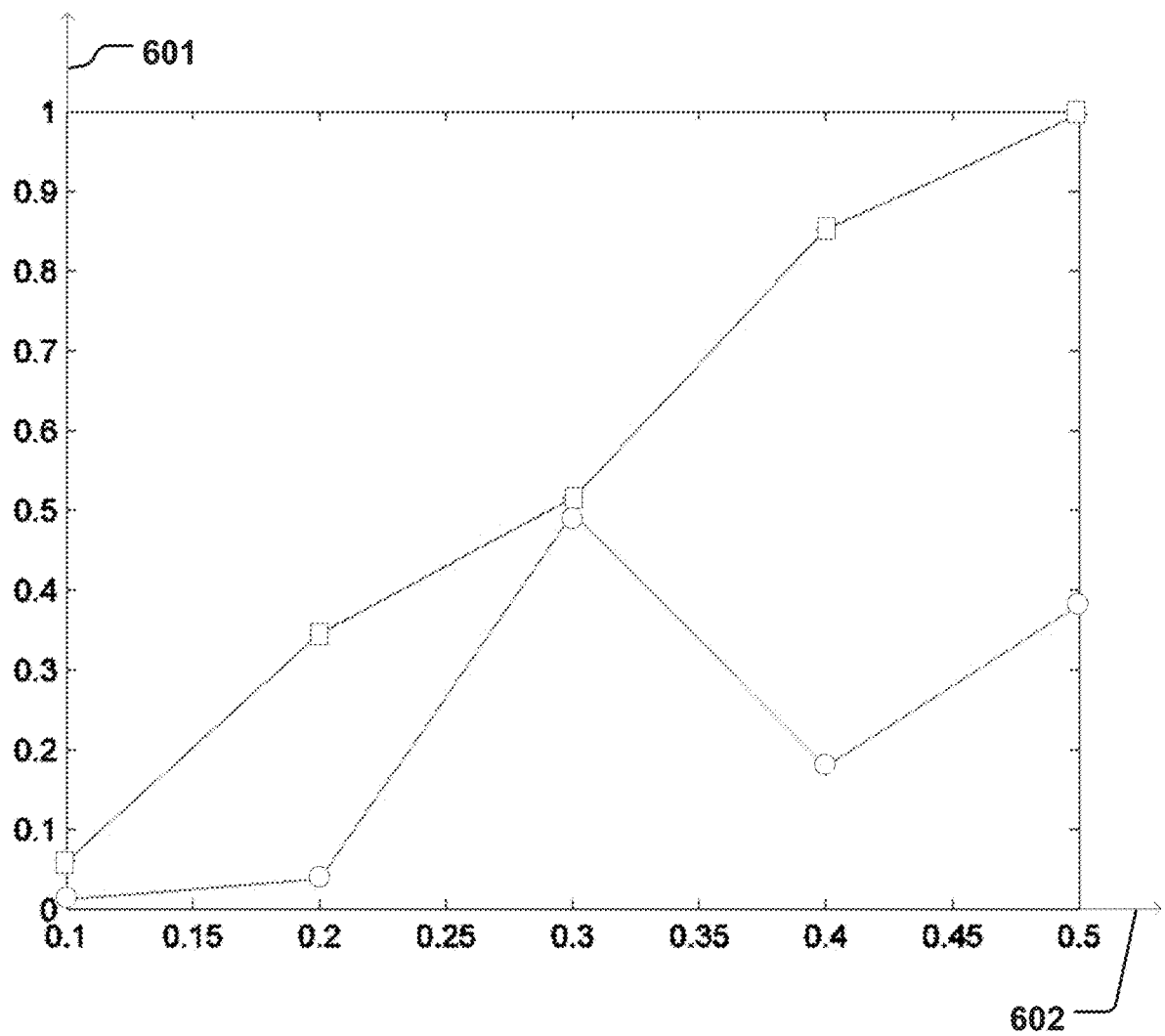
FIG. 6 is a schematic illustration of results obtained according to an embodiment of the present invention.

The fixation means 116 may be arranged to allow for connecting the ultrasonic transducer 115 to the probe support 101 at different distances from the magnet 102, 103. The distance may be variable along the axial direction 105 to optimize the excitation signal. The displacement of the nanoparticles is dependent on the distance between the magnet 102, 103, and the inserts 401, 402, 403. FIGS. 5a-f illustrates the displacement amplitude of the nanoparticles versus frequency for various concentrations of the inserts and for two different distances between the magnet and the inserts. The triangles represent the measurement values from the probe assembly 100 with the magnet 102, 103, close to the sample, the squares represent the same setup but the magnet 102, 103, is 3 mm farther away from the inserts, and the circles represent the prior art electromagnetic coil setup. Each symbol is a mean value of three cross-sections and the standard deviation is marked with error bars. It can be seen from FIGS. 5a-f that the probe assembly 100 induces a higher displacement than the prior art electromagnetic coil setup. The highest displacement is achieved when the magnet 102, 103, is close to the phantom/inserts (triangles). The increased displacement amplitude of the nanoparticles with the probe assembly 100 according to the present invention is also seen from FIG. 6, showing the measured displacement amplitude on axis 601 versus nanoparticle concentration on axis 602 for the probe assembly 100 (squares) and the prior art electromagnetic coil setup (circles). The probe assembly 100 provides accordingly for detection with a better signal to background ratio, which enhances e.g. the imaging and analysis of samples with low nanoparticle concentration. From FIG. 6 it is again seen that the laterally inhomogeneous magnetic field of the prior art setup gives a non-linear dependence of the displacement amplitude on the nanoparticle concentration, where the insert 402 with a concentration of 0.3 mg $Fe_3O_4$/ml has the highest displacement. This is in contrast to the more linear dependence obtained with the present imaging probe assembly 100 as seen in FIG. 6 (squares).

The arrangement of the magnet 102, 103, on the probe support 101 according to the above disclosure further reduces the influence of the axial coordinate in the axial direction 105 of the image plane 104 on the displacement amplitude. Hence a more accurate detection of the displacement amplitude is possible also in this direction of the image plane 104.

The imaging probe assembly 100 may comprise the ultrasound transducer 115, being arranged adjacent said magnet 102, 103. It should be realized that the inventive features as described above provides the aforementioned advantages irrespectively of the probe assembly 100 functions as a "snap-on" accessory to existing ultrasound transducers/probes, or has an ultrasound transducers/probe fixedly mounted to the probe support 101 as part of the probe assembly 100. In each case the probe support 101 provides for fixating the position of the ultrasonic transducer 115 in relation to the magnet 102, 103, which may be movably mounted on the probe support 101 to thereby create a time-varying magnetic field at the imaging plane 104 of the ultrasonic transducer 115. Alternatively or in addition the probe support 101 provides for fixating the position of the ultrasonic transducer 115 in relation to the magnet 102, 103, such that the magnet 102, 103, extend along the width of the imaging plane 104.

The magnet 102, 103, may be rotationally arranged on the probe support 101 and adjacent the ultrasound transducer 115 when connected to the probe support 101. The motion may thereby be a rotating motion. By rotating the magnet 102, 103, the magnetic field at the target location 110 is varied. The magnetic poles, N and S, of a permanent magnet 102, 103, may thus be displaced over time from a target location 110 at the imaging plane 104 by the motion of the magnet 102, 103, and thereby create a fluctuation in the magnetic field (T). The displacement may be provided by the aforementioned rotating motion, or any other motion that provides an oscillation of the magnetic field (T) over time at the target location 110. Hence, the magnetic poles (N, S) of the permanent magnet 102, 103, are upon said motion displaceable from a target location 110 in the imaging plane 104 with an oscillating motion.

As illustrated in FIG. 2 the magnet 102, 103, may comprise a first 102 and a second magnet 103, each being rotationally arranged on the probe support 101 and adjacent the ultrasound transducer 115, when connected to the probe support 101. Having a first 101 and a second 102 magnet may provide for an improved laterally homogeneous time-varying magnetic field (T). The first 102 and second 103 magnets may be rotatable in opposite directions, as illustrated by arrows ($w_1$, $w_2$) in FIG. 2. Alternatively, each of the first 102 and second 103 magnets may be rotatable in a direction opposite to that illustrated in FIG. 2, i.e. the first 102 and second 103 magnets would still be rotated in opposite directions in such case. As illustrated, the poles of each permanent magnet are arranged to rotate such that identical poles are facing each other to create a magnetic field gradient along the imaging plane 104. E.g. the N-poles of magnets 102, 103, are momentarily facing each other in the situation shown in FIG. 2. Subsequent rotation of the magnets 102, 103, will position the S-poles towards each other, and during the rotation the magnetic field at the target location 110 will undergo a fluctuation to move the magnetic particles. It may be conceivable that such fluctuation may be possible to generate from moving or oscillating a different number of magnets in relating to each other, and with oscillations in various directions. The symmetry of the arrangement illustrated in FIG. 2 may provide for an optimal time-varying magnetic field (T) at a target location 110 in the imaging plane 104. The imaging and analysis of an object at the target location 110 may thus be accurately performed, and further without influence from undesired lateral gradients in the magnetic field (T) as described above.

The probe support 101 may be adapted to connect to, and fixate the position of, an ultrasonic transducer 115 such that the imaging plane 104 of the ultrasonic transducer 115 extends along the axial direction 105 between the first 102 and second 103 magnets, as seen in FIG. 2. The first 102 and second 103 magnets are thus positioned on either side of the imaging plane 104 to provide a homogeneous time-varying magnetic field (T). The distance between the first magnet 102 and the imaging plane 104 may be the same as the distance between the second magnet 103 and the imaging plane 104. The first 102 and second 103 magnets have respective first and second rotational axes 106, 107, spanning, and being separated along, a plane 108. The axial direction 105 may be substantially normal to the plane 108, and/or the rotational axes 106, 107, may be substantially parallel to the lateral direction 118. This may further provide for a time-varying magnetic field (T) that has a minimal amount of undesired gradients. The nanoparticles will be displaced with an amplitude that is extending along the axial direction 105 of the ultrasound image plane 104. The rotational axes 106, 107, of magnets 102, 103, may thus extend in the plane 108 so that the distance from each of the magnets 102, 103, to a distal portion 109 of the ultrasonic transducer 115 is the same if the magnets 102, 103, have a uniform cross-sectional dimension along the rotational axes 106, 107. This provides for a time-varying magnetic field (T) that has the same characteristics along the width 119 of the imaging plane 104, where the width extends in the same direction as the rotational axes 106, 107. The relative positions of the magnets 102, 103, and the ultrasound transducer 115, when fixed to the probe support 101, may be varied to provide for customization according to the particular imaging application and thereby optimized to such varying applications. Hence it may be conceivable to vary the angle between the ultrasound transducer 115 and the plane 108 defined by the rotational axes 106, 107, and vary the distance between the magnets 102, 103.

Further, the probe support 101 may be adapted to connect to, and fixate the position of, an ultrasonic transducer 115 such that a distal portion 109 of said ultrasonic transducer is arranged between the first 102 and second magnets 103 when connected to the probe support 101, as illustrated in FIG. 2, to provide for an adequate detection signal. The distance between the distal portion 109, 120, i.e. the transducer face, and the plane 108 may be varied for example by either lowering or raising the ultrasonic transducer 115 along a height variable fixation means 116 in the probe support 101. The ultrasound transducer 115 may thus be positioned at varying vertical locations in the magnetic field (T) produced by the magnets 102, 103. As mentioned above, further relative adjustments may be possible, to position the transducer 115 and imaging plane 104 in any location of the magnetic field (T).

As discussed above, the first 102 and second 103 magnets may extend substantially along the width 119 of the imaging plane 104. The magnetic field may accordingly be homogeneous along the entire width of the imaging plane 104 to improve the imaging abilities.

As illustrated in FIG. 2, each of the first 102 and second 103 magnets may comprise cylindrically shaped magnets 102, 103, having respective first and second rotational axes 106, 107, extending in a lateral direction (118) and each having opposite magnetic poles (N, S) separated along a diameter of each of the magnets in the radial direction (r), whereby rotation of the magnets 102, 103, create a time-varying magnetic field (T) from each of the magnets 102, 103, at the target location 110. It is conceivable that other shapes of the magnets 102, 103, may provide the same effect.

The magnetomotive imaging probe assembly 100 may comprise a control unit 111 and a motor 112. The motor 112 is coupled to the control unit 111 and to the magnet 102, 103, to power the motion of the magnet 102, 103. The control unit 112 may be adapted to vary the speed of motion ($w_1$, $w_2$) of the magnet 102, 103, according to a predetermined pattern to thereby vary the frequency of the time-varying magnetic field (T) as a predetermined frequency impulse to generate a frequency impulse response of magnetic nanoparticles at the target location 110. This provides for determining an impulse response from the nanoparticles that may be indicative of the material properties, such as viscosity and density. Hence the nanoparticles may be displaced by the magnetic impulse and the material properties will affect how the displacement varies over time, such as the dominant frequency, maximum amplitude, and speed of damping may be indicative of material density, the elasticity and viscosity.

The control unit 112 may be adapted to vary the speed of motion $w_1$, $w_2$) of the magnet 102, 103, such as by increasing the speed linearly up to a certain maximum speed, and thereafter decrease the speed, to provide a sweep throughout frequencies and detect the resulting displacement amplitude of the nanoparticles. The control unit 112 may thus be adapted to vary the speed of motion ($w_1$, $w_2$) of the magnet 102, 103, according to such predetermined pattern to provide for detection of a frequency impulse response. The control unit may be adapted to set a constant speed of motion ($w_1$, $w_2$) of the magnet 102, 103. The control unit 112 may thus employ a magnetic force compensating control signal that varies the momentum of each of the magnets 102, 103, such that the varying magnetic force between the N and S poles of the magnets 102, 103, is compensated to provide for a constant rotational speed. Otherwise the angular speed may not be kept constant, as the magnetic S-pole of first magnet 102 has a tendency to lock to the magnetic N pole of the second magnet 103 due to the magnetic force between the poles. Depending on the position of the S-pole relative the N-pole during rotation of the magnets the magnetic force will vary, which thus may be compensated by the control unit 111.

The control unit 112 may be further adapted to synchronize the frequency or speed of motion ($w_1$, $w_2$) of the magnets 102, 103, to the ultrasound imaging in order to provide for ultrasound detection at the correct frequency, and further to allow for detection at the right phase relative the ultrasound imaging.

The ultrasound transducer 115 also has an ultrasound control unit 114 that provides for the necessary control and analysis related to the ultrasound equipment.

Figure 3:
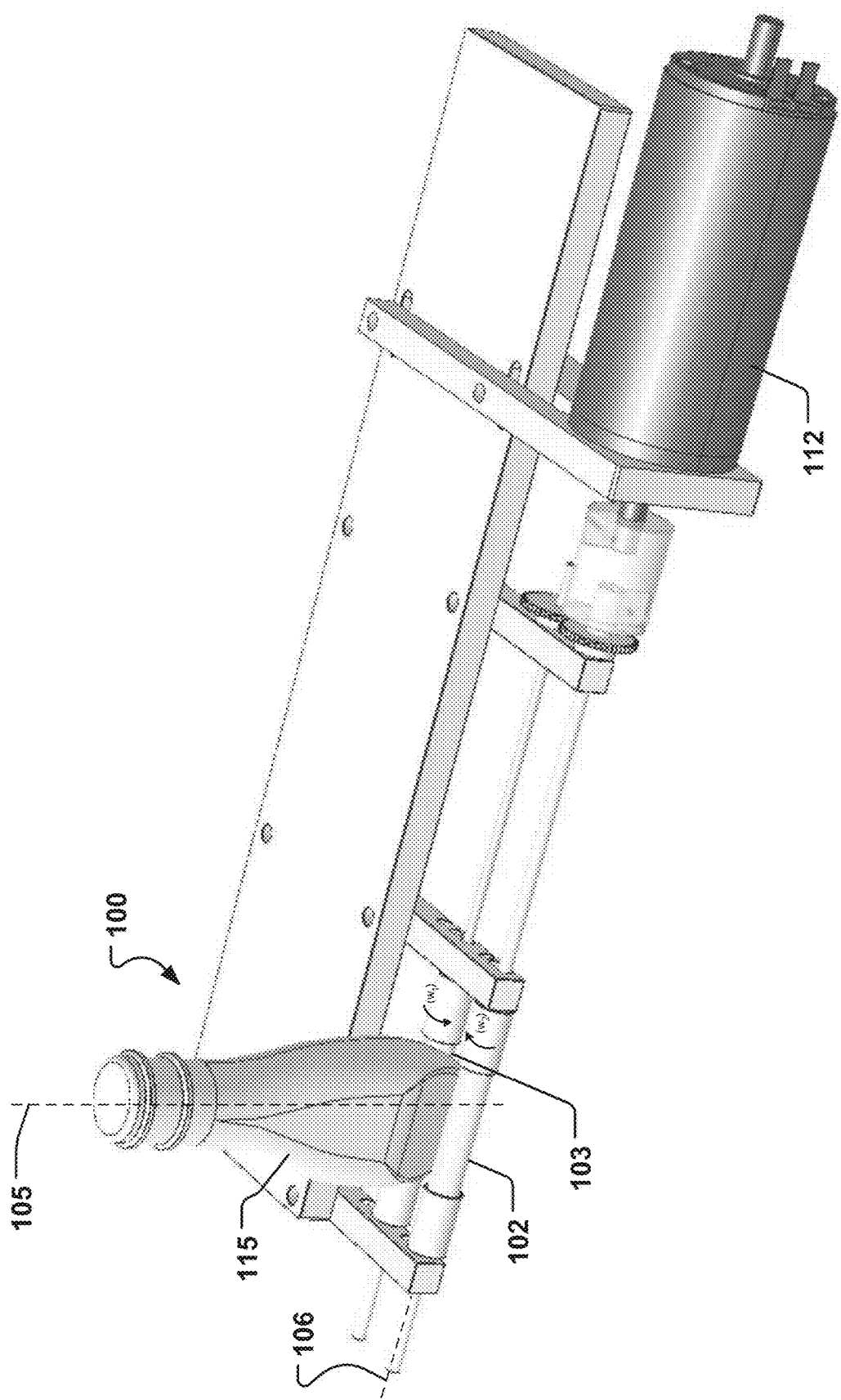
FIG. 3 is a schematic illustration of a magnetomotive imaging probe assembly according to an embodiment of the present invention.

FIG. 3 illustrates a schematic of an example of a probe assembly 100, showing the magnets 102, 103, connected to a motor 112, and an ultrasonic transducer 115. The probe support 101 has been omitted for clarity of presentation. FIG. 4 illustrates a schematic of another example of a probe assembly 100 showing the ultrasonic transducer 115 and magnets 102, 103, fixated in a probe support 101, which also may function as a casing of the probe assembly to isolate any subject to be imaged from the interior of the probe assembly 100, i.e. the magnets will be in the casing for avoiding interference with the subject.

Figure 9:
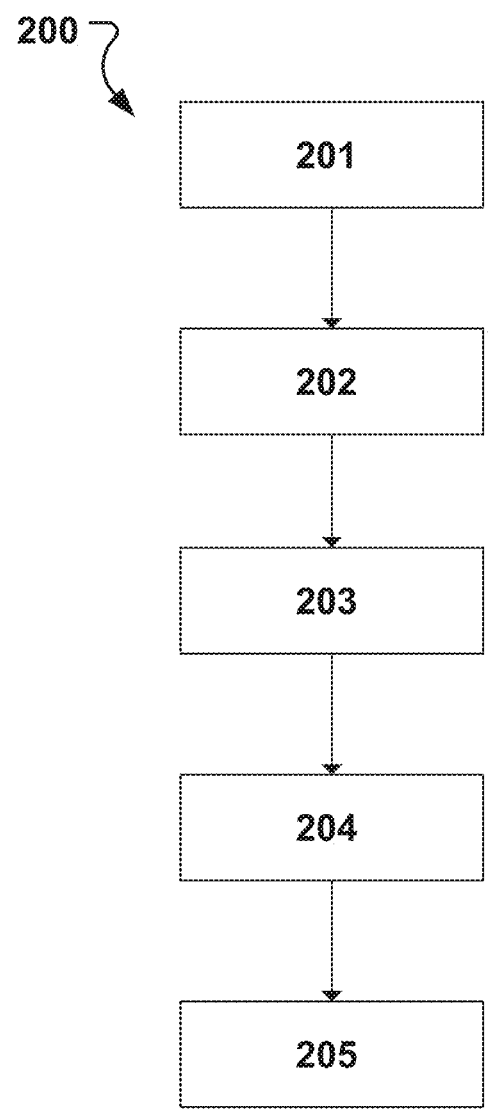
FIG. 9 is a flow chart illustrating a method according to an embodiment of the present invention.

FIG. 9 illustrates a flow-chart of a method 200 of magnetomotive imaging with a probe assembly 100, the probe assembly 100 comprising a probe support 101 adapted to connect to an ultrasound transducer 115 and a magnet 102, 103, movably arranged on the probe support 101. The method 200 comprises rotating 201 the magnet 102, 103, to generate a time-varying magnetic field (T) at an imaging plane 104 of the ultrasound transducer 115 when connected to the probe support 101. The method further comprises detecting 205 motion of magnetic nanoparticles in response to the time-varying magnetic field with the ultrasound transducer 115 in the imaging plane 104. As mentioned above, this provides for an accurate determination of nanoparticle concentration, and further improved analysis of the examined material.

The method 200 may comprise rotating 202 first 102 and second 103 cylindrical permanent magnets, each having opposite magnetic poles (N, S) separated along a diameter of each of said magnets in the radial direction (r), in opposite rotational directions on either side of the imaging plane.

The method 200 may comprise rotating 203 first 102 and second 103 cylindrical permanent magnets according to a predetermined pattern to thereby vary the frequency of said time-varying magnetic field (T) as a predetermined frequency impulse to generate a frequency impulse response of the magnetic nanoparticles. The properties of the material of the analyzed object may thus me determined. The predetermined pattern may for example include rotating the magnets with a certain number of turns, or fractions of turns, such as half a turn, during a period of time such as a certain number, or fractions of seconds or minutes, to subsequently detect the response from the nanoparticles.

The method 200 may alternatively or in addition comprise rotating 204 first 102 and second 103 cylindrical permanent magnets with a constant rotational speed.

The magnetomotive imaging probe assembly 100 according to the above disclosure may be used for magnetomotive ultrasound imaging of magnetic nanoparticles.

Figure 10:
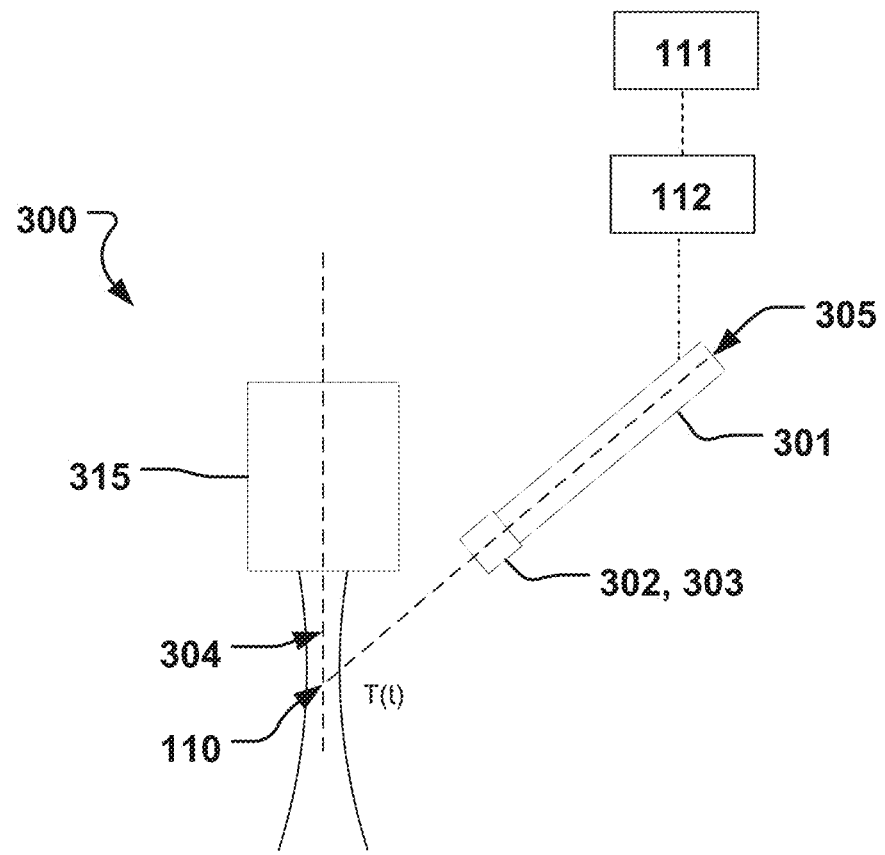
FIG. 10 is a schematic illustration of a magnetomotive imaging probe according to an embodiment of the present invention.

FIG. 10 illustrates a magnetomotive imaging probe system 300 of the present invention. The system 300 comprises a movable probe 301, a magnet 302, 303, arranged on the probe, and an ultra sound transducer 315. The magnet 302, 303, is arranged to generate a time-varying magnetic field (T) at an imaging plane 304 of the ultrasound transducer 315, distally of the ultra sound transducer 315 and the probe 301, when the probe 301 has a proximal first position 305 adjacent the ultra sound transducer 315. Since the probe is movable it can be freely positioned in various positions relative the ultra sound transducer 315, which allows for probing different regions in the imaging plane 304, i.e. displacing the magnetic particles in various regions and in different directions in the imaging plane 304. This facilitates and optimizes detection in the region of interest, thereby improving accuracy and extraction of material properties in targeted region. Further, since the ultra sound transducer 315 may also be moved to various positions relative the analysed object, the system 300 provides for improved flexibility e.g. during surgery when it is desired to characterize a tissue region of a complex anatomy. Having the probe 301 in a proximal position 305 adjacent the ultra sound transducer, and arranged to generated the time-varying magnetic field (T) distally of the ultrasound transducer and the probe 301, improved imaging and tissue characterization is provided for when frequent repositioning in relation to the object and/or the region of interest is required, such as in aforementioned complex anatomies or procedures involving several interventions at several target sites and regions of interest. Both the probe 301 and the ultra sound transducer 315 may thus be positioned proximally of the analysed object, and being movable in relation thereto, and without limitation with respect to the size of analysed object.

The probe 301 may thus be movable in relation to the ultra sound transducer 315, and the probe may be a handheld probe 301.

The magnet 302, 303, may be movably arranged on the probe 301, whereby in use, the magnet 302, 303, is arranged to generate said time-varying magnetic field (T) in response to a motion of the magnet relative the ultrasound transducer 315. Thus, the magnet 302, 303, may be a permanent magnet, with the previously aforementioned advantages as described for the embodiments relating to FIGS. 2-9. The magnet may comprise a first magnet 302, and a second magnet 303 as described in FIG. 2 with reference to first and second magnets 102, 103. Alternatively, a single magnet may be used, movably arranged in the probe 301. Generally, the magnet 302, 303, may have any arrangement as described for the embodiments relating to FIGS. 2-9, with the added feature in the system 300 of FIG. 10 that the magnet 302, 303, is repositionable in relation to the ultrasound transducer 315, by being arranged on a movable probe 301 as described previously.

The magnet 302, 303, may be displaceable from a target location 110 in the imaging plane 304 with an oscillating motion. This may provide for improved imaging and/or characterization of the analysed object at the target location 110. It may also provide for a compact and easy to use probe 301. Alternatively or in addition the magnet 302, 303, may have a rotating motion relative the probe 301, as described in relation to FIG. 2.

Alternatively the magnet 302, 303, may be an electromagnet.

The system 300 may comprise a control unit 111 and a motor 112 coupled to the probe 301. The motor being coupled to the control unit and to the magnet 302, 303, to power a motion of the magnet, wherein the control unit is adapted to vary the speed of motion ($w_1, w_2$) of the magnet 302, 303, according to a predetermined pattern to thereby vary the frequency of said time-varying magnetic field (T) as a predetermined frequency impulse to generate a frequency impulse response of magnetic nanoparticles at the target location 110, as described previously. Alternatively or in addition the control unit may be adapted to set a constant speed of motion ($w_1, w_2$) of the magnet 302, 303.

Figure 11:
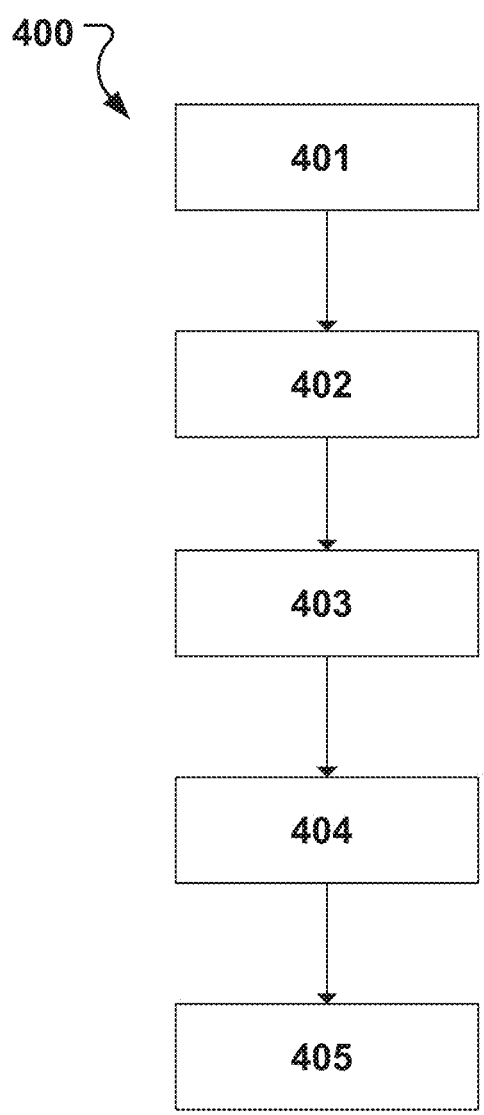
FIG. 11 is a flow chart illustrating a method according to an embodiment of the present invention.

FIG. 11 illustrates a method 400 of magnetomotive imaging with a probe system 300 comprising a movable probe 301 and an ultra sound transducer 315, and a magnet 302, 303 arranged on the probe. The method 400 comprises; positioning 401 the probe at a proximal first position 305 adjacent the ultra sound transducer, generating 402, with the magnet, a time-varying magnetic field (T) at an imaging plane 104 of the ultrasound transducer, distally of the ultra sound transducer and the probe, and detecting 403 motion of magnetic nanoparticles in response to the time-varying magnetic field with the ultrasound transducer in said imaging plane.

Generating the time-varying magnetic field (T) may comprise moving 404 the magnet 302, 303, relative the ultrasound transducer 315. Moving the magnet 302, 303, may comprise displacing 405 the magnet 302, 303, from a target location 110 in the imaging plane 304 with an oscillating motion.

As will be appreciated by one of skill in the art, the present invention may be embodied as device, system, or method.

The present invention has been described above with reference to specific embodiments. However, other embodiments than the above described are equally possible within the scope of the invention. Different method steps than those described above, may be provided within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A magnetomotive imaging probe system for imaging magnetic particles where said magnetic particles are displaced due to a time varying magnetic field, comprising:

a movable probe,
a magnet arranged on said probe, and
an ultrasound transducer,
wherein said magnet is arranged to generate said time-varying magnetic field at an imaging plane of said ultrasound transducer, distally of said ultrasound transducer and said probe, when said probe has a proximal first position adjacent said ultrasound transducer;
wherein the magnet is movably arranged on the probe and adapted to have a motion which generates said time-varying magnetic field;
wherein the system comprises a control unit and a motor, said motor being coupled to the control unit and to the magnet to power said motion of said magnet, wherein said control unit is adapted to vary the speed of motion of said magnet according to a predetermined pattern to thereby vary the frequency of said time-varying magnetic field as a predetermined frequency impulse to generate a frequency impulse response of said magnetic particles in said imaging plane of said ultrasound transducer; and the varied magnetic field causes the magnetic particles in the imaging plane of the ultrasound transducer to move or oscillate where the movement is detected by the ultrasound transducer and used for analyzing tissue in the imaging plane of the ultrasound transducer.

2. A method of magnetomotive imaging with a probe system comprising a movable probe and an ultrasound transducer, and a magnet arranged on said probe and the system further comprises a control unit and a motor, said motor being coupled to the control unit and to the magnet to power a motion of said magnet, said method comprising:
positioning said probe at a proximal first position adjacent said ultrasound transducer,
generating, with said magnet, a time-varying magnetic field at an imaging plane of said ultrasound transducer, distally of said ultrasound transducer and said probe,
detecting motion of magnetic particles in response to said time-varying magnetic field with said ultrasound transducer in said imaging plane, wherein the motion detected is used for analyzing tissue in the imaging plane of the ultrasound transducer;
moving the magnet on the probe and whereby a motion of the magnet generates the time-varying magnetic field; and
varying the speed of motion of said magnet by the control unit connected to the motor according to a predetermined pattern to thereby vary the frequency of said time-varying magnetic field as a predetermined frequency impulse to generate a frequency impulse response of magnetic particles in said imaging plane of said ultrasound transducer, or wherein a constant speed of motion of said magnet is set by said control unit.

3. A magnetomotive imaging probe assembly comprising:
a probe support, and a magnet movably arranged on said probe support and connected to said probe support,
an ultrasound transducer for imaging tissue at an imaging plane by sending and receiving an ultrasound signal;
wherein said probe support is connected to said ultrasound transducer to fixate a position of said ultrasound transducer in relation to, and adjacent, said magnet, whereby in use, said magnet is arranged to generate a time-varying magnetic field in response to a motion of said magnet at an imaging plane of said ultrasound transducer and said time-varying field is adapted to displace magnetic particles at an imaging plane of said ultrasound transducer to be detected by said ultrasound transducer in said imaging plane for analyzing tissue in the imaging plane of the ultrasound transducer; and
wherein said magnet is rotationally arranged on said probe support to provide a rotational movement and wherein said rotational movement is said motion that provides said time-varying magnetic field.

4. The magnetomotive imaging probe assembly according to claim 3, wherein said magnet is arranged on said support to extend parallel to a lateral direction, and wherein said probe support is adapted to connect to, and fixate the position of, an ultrasonic transducer such that the width of said imaging plane extend in said lateral direction, whereby said magnet is arranged to extend along the width of said imaging plane.

5. The magnetomotive imaging probe assembly according to claim 3, wherein said imaging probe assembly comprises said ultrasound transducer, being arranged adjacent said magnet.

6. The magnetomotive imaging probe assembly according to claim 3, wherein said magnet is a permanent magnet.

7. The magnetomotive imaging probe assembly according to claim 6, wherein the magnetic poles of said permanent magnet, upon said motion, are displaceable from a target location in said imaging plane with an oscillating motion.

8. The magnetomotive imaging probe assembly according to claim 3, wherein said magnet comprises a first and a second magnet, each being rotationally arranged on said probe support and adjacent said ultrasound transducer, when connected to said probe support.

9. The magnetomotive imaging probe assembly according to claim 8, wherein first and second magnets are rotatable in opposite directions.

10. The magnetomotive imaging probe assembly according to claim 9, wherein said each of said first and second magnets comprises cylindrically shaped magnets having respective first and second rotational axes extending in a lateral direction and each having opposite magnetic poles separated along a diameter of each of said magnets in a radial direction (r), whereby rotation of said magnets create said time-varying magnetic field from each of said magnets at said target location.

11. The magnetomotive imaging probe assembly according to claim 8, wherein said probe support is adapted to connect to, and fixate said position of, said ultrasonic transducer such that said imaging plane of said ultrasonic transducer extends along an axial direction between said first and second magnets.

12. The magnetomotive imaging probe assembly according to claim 11, wherein said first and second magnets have respective first and second rotational axes spanning, and being separated along, a plane, and wherein said axial direction is substantially normal to said plane.

13. The magnetomotive imaging probe assembly according to claim 8, said probe support is adapted to connect to, and fixate said position of, an ultrasonic transducer such that a distal portion of said ultrasonic transducer is arranged between said first and second magnets when connected to said probe support.

14. The magnetomotive imaging probe assembly according to claim 3, comprising a control unit and a motor, said motor being coupled to said control unit and to said magnet to power said motion of said magnet, wherein said control unit is adapted to vary a speed of motion of said magnet according to a predetermined pattern to thereby vary a frequency of said time-varying magnetic field as a predetermined frequency impulse to generate a frequency impulse response of magnetic particles at said target location, or wherein said control unit is adapted to set a constant speed of motion of said magnet.

15. A method of magnetomotive imaging of tissue with a probe assembly comprising a probe support connected to an ultrasound transducer, and a magnet movably arranged on said probe support and connected to the probe support, said method comprising:
   rotating said magnet to generate a time-varying magnetic field at an imaging plane in said tissue of said ultrasound transducer; and
   detecting motion of magnetic particles in response to said time-varying magnetic field with said ultrasound transducer in said imaging plane, wherein the motion detected is used for analyzing tissue in the imaging plane of the ultrasound transducer.

* * * * *